(12) United States Patent
van Platerink

(10) Patent No.: US 8,618,249 B2
(45) Date of Patent: Dec. 31, 2013

(54) PEPTIDES HAVING AN ACE INHIBITING EFFECT

(75) Inventor: Christianus Jacobus van Platerink, Vlaardingen (NL)

(73) Assignee: DSM IP Assets B.V., Heerlen (NL)

( * ) Notice: Subject to any disclaimer, the term of this patent is extended or adjusted under 35 U.S.C. 154(b) by 292 days.

(21) Appl. No.: 13/179,078

(22) Filed: Jul. 8, 2011

(65) Prior Publication Data

US 2011/0263506 A1      Oct. 27, 2011

Related U.S. Application Data

(63) Continuation of application No. 11/919,392, filed as application No. PCT/EP2006/003263 on Mar. 31, 2006, now abandoned.

(30) Foreign Application Priority Data

Apr. 28, 2005  (EP) .................................... 05076050
Jan. 24, 2006  (EP) .................................... 06075140

(51) Int. Cl.
*C07K 5/08*         (2006.01)

(52) U.S. Cl.
USPC .......................... 530/331; 514/21.9; 514/16.2

(58) Field of Classification Search
USPC .................................. 530/331; 514/21.9, 16.2
See application file for complete search history.

(56) References Cited

U.S. PATENT DOCUMENTS

| 4,216,209 | A  | * | 8/1980  | Bellini et al. ................ 514/15.7 |
| 4,293,481 | A  | * | 10/1981 | Condon et al. ................ 530/331 |
| 7,579,315 | B2 | * | 8/2009  | Smith ............................. 514/1.1 |
| 7,833,985 | B2 | * | 11/2010 | Ogura et al. ................. 514/18.4 |

* cited by examiner

*Primary Examiner* — David Lukton
(74) *Attorney, Agent, or Firm* — Morgan, Lewis & Bockius LLP

(57) ABSTRACT

Use of the tripeptide ITP and salts thereof for the preparation of a functional food angiotensin-converting enzyme inhibitor. Also provided is the use of the combination of tripeptide MAP and the tripeptide ITP and salts thereof as an angiotensin-converting enzyme inhibitor in functional foods.

13 Claims, No Drawings

PEPTIDES HAVING AN ACE INHIBITING EFFECT

CROSS REFERENCE TO RELATED APPLICATION

This application is a continuation of and claims priority benefit from U.S. patent application Ser. No. 11/919,392, filed 26 Oct. 2007, now abandoned, which in turn is a National Stage Entry of International Patent Application No. PCT/EP2006/003263, filed 31 Mar. 2006, now published as WO 2006/114192, which in turn claims priority benefit from European Patent Application No. 05076050.3, filed 28 Apr. 2005, and European Patent Application No. 06075140.1, filed 24 Jan. 2006, all of which are incorporated herein by reference in their entirety.

FIELD OF THE INVENTION

The invention relates to certain peptides for the preparation of a functional food angiotensin-converting enzyme (ACE) inhibitor. Also provided is the use of the tripeptide ITP and salts thereof as an angiotensin-converting enzyme inhibitor in functional foods.

BACKGROUND TO THE INVENTION

Hypertension or high blood pressure is considered to be one of the main risk factors for Cardio Vascular Diseases (CVD). One of the mechanisms which regulates blood pressure is the renin-angiotensin system. This is a cascade of reactions leading to the formation of angiotensin II, which has a strong vasoconstrictive and hence blood pressure increasing effect. Inhibition of one of the key enzymes in this cascade: Angiotensin I Converting Enzyme (ACE) reduces formation of angiotensin II and thus has a blood pressure lowering effect. Long term human intervention studies have shown regular intake of low amounts of ACE inhibitors reduces CVD by 25% (Gerstein et al. (2000), The Lancet 355, 253-259).

ACE-inhibitors in food products are well known. Such food products have for instance been prepared by fermentation of milk or milk products. In a placebo-controlled study, the blood pressure lowering effect of VPP and IPP in sour milk was shown in hypertensive humans (Hata, Y et al. (1996), American Journal of Clinical Nutrition 64, 767-771).

A commercially available fermented milk product, which claims to be "suitable for those with mild hypertension" is Calpis sour milk, fermented with *Lactobacillus helveticus* and *Saccharomyces cervisiae*, produced by Calpis Food Industry, Japan. Another commercially available fermented milk product is Evolus produced by Valio, Finland. These fermented milk products are fermented with *Lactobacillus helveticus* (*Lb. helveticus*) strains. The products contain bioactive peptides (VPP and IPP) which are produced by proteolysis of caseins and which showed in vitro ACE inhibition.

SUMMARY OF THE INVENTION

It is an object of the invention to provide a food product suitable for ACE inhibition. It is another object to provide such food products having a good taste, in particular reduced bitterness. It is a further object to provide a food product having a high concentration of ACE-inhibitor. One or more of these objects is attained according to the invention by the use of the tripeptide ITP and salts thereof, optionally in combination with the tripeptide MAP for the preparation of a functional food angiotensin-converting enzyme inhibitor.

Also provided according to a second aspect of the present invention is the use of the tripeptide ITP and salts thereof as an angiotensin-converting enzyme inhibitor in functional foods. A third aspect of the invention relates to the combined use of tripeptide MAP and tripeptide ITP as an angiotensin-converting enzyme inhibitor in functional foods.

"Functional food (product)s))" according to the present invention are defined as food products (including for the avoidance of doubt, beverages), suitable for human consumption, in which MAP and/or ITP is used as an ingredient in an effective amount, such that a noticeable health benefit for the consumer of the food product is obtained.

DETAILED DESCRIPTION OF THE INVENTION

The common one letter code is ordinarily used to describe amino-acids. MAP (Met-Ala-Pro) corresponds to beta-casein position 102-104, and ITP (Ile-Thr-Pro) to alpha-s2-casein position 119-121.

According to the invention, we have found that the tripeptides MAP and ITP have a high ACE-inhibiting effect, corresponding to a low IC50 value, respectively 0.4 for MAP and 10 for ITP (in $\mu M$) as determined in the experimental part herein. Moreover, we have found that both tripeptides MAP and ITP are stable in the human intestinal tract. The tripeptide MAP and/or the tripeptide ITP and salts thereof are therefore very suitable as an angiotensin-converting enzyme inhibitor, in particular in vivo in humans. The angiotensin-converting enzyme inhibitor is a functional food product.

The invention provides a food product suitable for angiotensin-converting enzyme inhibition comprising an amount of 0.5 mg/kg or more of MAP and/or 3 mg/kg or more of tripeptide ITP. Due to its ACE-inhibiting effect the food product according to the invention is capable of lowering the blood pressure of humans having elevated blood pressure, and is particularly suited to lowering blood pressure in humans having moderately elevated blood pressure. Preferably the food product comprises an amount of 1 mg/kg or more MAP and/or an amount of 6 mg/kg or more tripeptide ITP. More preferably the food product comprises 2 mg/kg or more MAP and/or 12 mg or more ITP, even more preferably 5 mg/kg to 20 mg/kg or more MAP and/or 25-100 mg/kg ITP. MAP is especially preferred because of its exceptionally low IC50 value. Preferably the food product comprises 12 mg or more ITP, even more preferably 25-100 mg/kg ITP. MAP and/or ITP may be made by hydrolysis or fermentation of any protein substrate containing the amino acid sequences MAP and/or ITP. Advantageously the protein substrate contains both amino acid sequences MAP and ITP.

Through optimisation of the fermentation or hydrolysis conditions, the production of the biologically active molecules MAP and/or ITP may be maximised. The skilled person trying to maximise the production will know how to adjust the process parameters, such as hydrolysis time, hydrolysis temperature, enzyme type and concentration etc.

For hydrolysate-optimisation, the identity of the precursors of the active peptides needs to be known. However, detection and identification of the biologically active peptides in complex hydrolysates or ferments is a challenging task. Typically, just a few biologically active peptides are present at relatively low levels in a complex sample containing thousands of peptides. Traditional identification approaches employing repeated cycles of high-performance liquid chromatographic (HPLC) fractionation and biochemical evaluation are generally time consuming and prone to losses of activity.

In the present work a continuous flow biochemical assay is coupled on-line to an HPLC fractionation system. The HPLC column effluent is split between a continuous flow ACE bioassay and a chemical analysis technique (mass spectrometry). Crude hydrolysates are separated by HPLC, after which the presence of biologically active compounds is detected by means of the on-line biochemical assay. Mass spectra are recorded continuously. Hence, structural information is immediately available when a peptide shows a positive signal on the biochemical assay.

Food products according to the invention are defined as products, suitable for human consumption. Preferably, according to the invention MAP and/or ITP is used as an ingredient in an effective amount, such that an ACE-inhibitory effect is obtained.

The food products according to the invention are preferably made according to a process involving the following steps:
(a) enzymatic hydrolysis of a protein substrate comprising hydrolysed protein product;
(b) separation from the hydrolysed protein product of a fraction rich in tripeptide MAP and/or the tripeptide ITP; and optionally
(c) concentrating and/or drying the fraction from step b) to obtain a solid rich in tripeptide MAP and/or the tripeptide ITP; and
(d) using the solid prepared in step c) as an ingredient in the preparation of the food product.

The enzymatic hydrolysis step (a) may be any enzymatic treatment of a suitable protein substrate leading to hydrolysis of the protein resulting in liberation of MAP and/or ITP.

Preferably the protein substrate may be any material that contains the amino acid sequence MAP and/or ITP. Protein substrates known to encompass MAP are, for example, casein, wheat gluten, isolate, egg protein, rice protein, quinoa protein, amaranth protein and sunflower protein. Examples of especially suitable substrates include whole milk, skimmed milk, (acid) casein or caseinate, rennet casein, acid whey products or cheese whey products.

Most preferably the protein substrate is casein or milk. milk, casein, casein powder, casein powder concentrates, casein powder isolates, or beta-casein, or alpha-s2-casein. Preferably a substrate that has a high content of casein, such as casein protein isolate (CPI) or caseinate.

The enzyme may be any enzyme that is able to hydrolyse protein substrate resulting in the liberation of one or more of MAP and/or ITP. Examples of a preferred enzyme A suitable hydrolysate containing MAP and ITP may be obtained by hydrolysis with an endo-protease and a tri-peptidase as described in WO03/102905.

The separation step (b) (or concentration step (b)) may be executed in any way known to the skilled person, e.g. by filtration, centrifugation or chromatography and combinations thereof. Preferably the separation step (b) is executed using an ultrafiltration (UF) and/or nanofiltration (NF) techniques. The pore size of the membranes used in the filtration step, as well as the charge of the membrane may be used to control the separation of the tripeptide MAP and/or the tripeptide ITP. The fractionation of casein protein hydrolysates using charged UF/NF membranes is described in Y. Poilot et al, Journal of Membrane Science 158 (1999) 105-114. Electrodialysis is for instance described in WO00/42066.

Most preferably the separation is executed using acid precipitation.

The drying step (c) involves drying the fraction from step b) to obtain a solid rich in tripeptide MAP and/or the tripeptide ITP. This step may be done in a conventional way, e.g. by spray drying or freeze drying.

In a preferred embodiment the product of the separation step is dried until a concentrated solution of hydrolysed protein, having a low Aw is obtained. In such way the formation of off-flavour through Maillard reactions may be avoided.

The fraction rich in peptides prepared in step (b) is hereafter designated as ACE-fraction and the solid prepared in step (c) is hereafter designated as ACE-solid. The ACE-fraction and/or the ACE-solid may advantageously be used as an ingredient in a food product.

The food product according to the invention or food products derived therefrom may be pasteurised or sterilised.

The food products according to the invention may be of any food type. They may comprise common food ingredients in addition to the food product, such as flavour, sugar, fruits, minerals, vitamins, stabilisers, thickeners, etc. in appropriate amounts.

Preferably, the food product comprises 50-200 mmol/kg $K^+$ and/or 15-60 mmol/kg $Ca^{2+}$ and/or 6-25 mmol/kg $Mg^{2+}$ more preferably, 100-150 mmol/kg and/or 30-50 mmol/kg $Ca^{2+}$ and/or 10-25 mmol/kg $Mg^{2+}$ and most preferably 110-135 mmol/kg $K^+$and/or 35-45 mmol/kg $Ca^{2+}$ and/or 13-20 mmol/kg $Mg^{2+}$. These cations have a beneficial effect of further lowering blood pressure when incorporated in the food products according to the invention.

Advantageously the food product comprises one or more B-vitamins. The B-vitamin is preferably one or more of folic acid, Vitamin B2, Vitamin B6, and Vitamin B12. Preferably the composition comprises all of the B-vitamins folic acid, Vitamin B2, Vitamin B6, and Vitamin B12.

Folic acid is the synthetic, stable form of naturally occurring folates. Folic acid is known to participate in the metabolism of homocysteine which is an amino acid in the human diet. High homocystein levels have been correlated to an increased risk of cardiovascular disease. It is thought that lowering homocysteine may reduce the risk of cardiovascular disease. Herein the term folic acid also includes folates.

Vitamins B6 and B12 are known to interfere with the biosynthesis of purine and thiamine, to participate in the synthesis of the methyl group in the process of homocysteine methylation for producing methionine and in several growth processes. Vitamin B6 (pyridoxine hydrochloride) is a known vitamin supplement. Vitamin B12 (cyanobalamin) contributes to the health of the nervous system and is involved in the production of red blood cells. It is also known as a vitamin in food supplements.

Because of their combined positive effect on cardiovascular disease risk reduction, it is preferred that products according to the invention comprises vitamin B6 and vitamin B12 and folic acid.

The amount of the B-vitamins in the food product may be calculated by the skilled person based daily amounts of these B-vitamins given herein: Folic acid: 200-800 µg/day, preferably 200-400 µg/day; Vitamin B6: 0.2-2 mg/day, preferably 05-1 mg/day and Vitamin B12: 0.5-4 µg/day, preferably 1-2 µg/day.

Preferably, the food product comprises one or more phytosterols, phytostanols and/or analogues or derivatives thereof.

Typically, the phytosterols, phytostanols and their analogues and derivatives may be selected from one or more of phytosterols, phytostanols, synthetic analogues of phytosterols and phytostanols and esterified derivatives of any of the foregoing, and mixtures of any of these. The total amount of such substances in a food product or food supplement is preferably from 0.01% to 20%, more preferably from 0.1% to 15%, still more preferably from 0.2% to 8%, and most preferably from 0.3% to 8% by weight of the food product composition.

Preferably, the daily intake of such sterol-type component of the combination is from 0.1 g to 3 g, more preferably from 1.5 g to 2.5 g, especially from 2 g to 2.25 g per day.

Phytosterols, also known as plant sterols or vegetable sterols can be classified in three groups, 4-desmethylsterols, 4-monomethylsterols and 4,4'-dimethylsterols. In oils they mainly exists as free sterols and sterol esters of fatty acids although sterol glucosides and acylated sterol glucosides are also present. There are three major phytosterols namely beta-sitosterol, stigmasterol and campesterol. Schematic drawings of the components meant are as given in "Influence of Processing on Sterols of Edible Vegetable Oils", S. P. Kochhar; *Prog. Lipid Res.* 22: pp. 161-188.

The phytostanols are the respective 5α-saturated derivatives of phytosterols such as sitostanol, campestanol and their derivatives.

Synthetic analogues of any of the phytosterols or phytostanols (which include chemically modified natural phytosterols or phytostanols) may be used.

Preferably the phytosterol or phytostanol is selected from the group comprising fatty acid ester of β-sitosterol, β-sitostanol, campesterol, campestanol, stigmasterol, stigmastanol and mixtures thereof.

The optional phytosterol or phytostanol materials recited above may optionally be provided in the form of one or more fatty acid esters thereof. Mixtures of esterified and non-esterified materials may also be used.

Thus, any of the phytosterols, phytostanols and their synthetic analogues used in the present invention are preferably esterified with a fatty acid. Preferably, they are esterified with one or more $C_{2-22}$ fatty acids. For the purpose of the invention the term $C_{2-22}$ fatty acid refers to any molecule comprising a $C_{2-22}$ main chain and at least one acid group. Although not preferred within the present context the $C_{2-22}$ main chain may contain 1-6 double bonds, be partially substituted or side chains may be present. Preferably, however the $C_{2-22}$ fatty acids are linear molecules comprising one or two acid group(s) as end group(s). Most preferred are linear $C_{8-22}$ fatty acids as occur in natural liquid oils.

Suitable examples of any such fatty acids are acetic acid, propionic acid, butyric acid, caproic acid, caprylic acid, capric acid. Other suitable acids are for example citric acid, lactic acid, oxalic acid and maleic acid. Most preferred are lauric acid, palmitic acid, stearic acid, arachidic acid, behenic acid, oleic acid, cetoleic acid, erucic acid, elaidic acid, linoleic acid and linolenic acid.

When desired a mixture of fatty acids may be used for esterification of the sterols. For example, it is possible to use a naturally occurring fat or oil as a source of the fatty acid and to carry out the esterification via an interesterification reaction. Use of a natural source nearly always results in a mixture of fatty acids.

In a particular embodiment, the fatty acid mixture contains a high amount (>50%, preferably >70%, further preferred >80%) of unsaturates, being either monounsaturated fatty acids (MUFA) and/or polyunsaturated fatty acids (PUFA). This does not only provide the advantage of e.g. PUFA itself having good blood cholesterol lowering capacity, but also of the sterols esters prepared with such fatty acids.

Preferably fatty acid mixtures of sunflower, safflower, rapeseed, linseed, olive oil, linola and/or soybean are used. These are typical sources of high PUFA and/or low SAFA. Suitable esterification conditions are for example described in WO 92/19640.

The above described food ingredients, contributing to increasing cardiovascular health, K+, Ca2+ and Mg2+, B-vitamins (folic acid, B6, B12) and sterols are herein collectively referred to as heart health ingredients.

Preferably the food products according to the invention are drinks, more preferably fruit juice products or dairy drinks optionally with added fruit juice, dairy type products, frozen confectionary products or spreads/margarines. These preferred types of food products are described in some detail below and in the examples. Also suitable are baked goods such as cakes, biscuits and muffins, dairy type foods, snacks, etc.

Fruit Juice Products

Examples of fruit juice products according to the invention are juices derived from citrus fruit like orange and grapefruit, tropical fruits, banana, peach, peer, strawberry, to which ACE-solid and/or ACE-fraction and optionally one or more heart health ingredients are added.

Dairy Type Products

Examples of dairy products according to the invention are milk, dairy spreads, cream cheese, milk type drinks and yoghurt, to which ACE-solid and/or ACE-fraction and optionally one or more heart health ingredients are added.

The food product may be used as such as a milk type drink. alternatively flavour or other additives may be added. A dairy type product may also be made by adding ACE-solid and/or ACE-fraction to water or to a dairy product.

An example of a composition for a yoghurt type product is about 50-80 wt. % water, 0.1-15 wt. % ACE-solid and optionally one or more heart health ingredients, 0-15 wt. % whey powder, 0-15 wt. % sugar (e.g. sucrose), 0.01-1 wt. % yoghurt culture, 0-20 wt. % fruit, 0.05-5 wt. % vitamins and minerals, 0-2 wt. % flavour, 0-5 wt. % stabilizer (thickener or gelling agent). To the yoghurt, fruit may be added.

A typical serving size for a yoghurt type product could be from 50 to 250 g, generally from 80 to 200 g.

Frozen Confectionery Products

For the purpose of the invention the term frozen confectionery product includes milk containing frozen confections such as ice-cream, frozen yoghurt, sherbet, sorbet, ice milk and frozen custard, water-ices, granitas and frozen fruit purees.

Preferably the level of solids in the frozen confection (e.g. sugar, fat, flavouring etc) is more than 3 wt. %, more preferred from 10 to 70 wt. %, for example 40 to 70 wt. %.

Ice cream will typically comprise 0 to 20 wt. % of fat, 0.1 to 20 wt. % ACE-solid and optionally one or more heart health ingredients, sweeteners, 0 to 10 wt. % of non-fat milk components and optional components such as emulsifiers, stabilisers, preservatives, flavouring ingredients, vitamins, minerals, etc, the balance being water. Typically ice cream will be aerated e.g. to an overrun of 20 to 400%, more specific 40 to 200% and frozen to a temperature of from −2 to −200° C., more specific −10 to −30° C. Ice cream normally comprises calcium at a level of about 0.1 wt %.

Other Food Products

Other food product according to the invention can be prepared by the skilled person based on common general knowledge, MAP and/or ITP as such or in a protein hydrolysate and optionally one or more heart health ingredients in suitable amounts. Examples of such food products are baked goods, dairy type foods, snacks, etc.

Advantageously the food product is an oil and water containing emulsion, for instance a spread. Oil and water emulsion is herein defined as an emulsion comprising oil and water and includes oil in water (O/W) emulsions and water in oil emulsions (W/O) and more complex emulsions for instance water-in-oil-in-water (W/O/W/O/W) emulsions. Oil is herein defined as including fat. Preferably the food product is a spread, frozen confection, or sauce. Preferably a spread according to the invention comprises 30-90 wt. % vegetable oil. Advantageously a spread has a pH of 4.2-6.0.

EXAMPLES

Analysis Techniques

High Resolution Screening-Mass Spectrometry (HRS-MS)

MAP and ITP as novel ACE inhibiting peptides were identified in samples by using 2-dimensional-chromatographic-separation combined with an at-line ACE activity assay and mass spectrometry for identification. In the first analysis the peptide mixture is separated on an ODS3 liquid chromatography (LC) column. An activity profile is created from fractions collected from the analysis using a slightly modified Matsui assay. In the second analysis the fractions from the first column showing a high activity are further separated on a Biosuite LC column using a different gradient profile. The fractions collected from this second column are split into two parts, one part is used for the activity measurement while MS and MS-MS is applied on the other part for identification of the peptides present.

All analyses were performed using an Alliance 2795 HPLC system (Waters, Etten-Leur, the Netherlands) equipped with a dual trace UV-detector. For identification of the peptides the HPLC-system was coupled to a Q-TOF mass spectrometer from the same supplier.

20 μl of a 10% (w/v) solution of PH in Milli-Q water was injected on a 150×2.1 Inertsil 5 ODS3 column with a particle size of 5 μm (Varian, Middelburg, the Netherlands). Mobile phase A consisted of a 0.1% trifluoroacetic acid (TFA) solution in Milli-Q water. Mobile phase B consisted of a 0.1% TFA solution in acetonitrile. The initial eluent composition was 100% A. The eluent was kept at 100% A for 5 minutes. Then a linear gradient was started in 10 minutes to 5% B, followed by a linear gradient in 10 minutes to 30% B. The column was flushed by raising the concentration of B to 70% in 5 minutes, and was kept at 70% B for another 5 minutes. After this the eluent was reduced to 100% A in 1 minute and equilibrated for 9 minutes. The total run time was 50 minutes. The effluent flow was 0.2 ml min$^{-1}$ and the column temperature was set at 60° C. A UV chromatogram was recorded at 215 nm. Eluent fractions were collected in a 96 well plate using a 1 minute interval time resulting in fraction volumes of 200 μl. The effluent in the wells was neutralised by addition of 80 μl of a 0.05% solution of aqueous ammonium hydroxide (25%). The solvent was evaporated until dryness under nitrogen at 50° C. After this the residue was reconstituted in 40 μl of Milli-Q water and mixed for 1 minute. Then 27 μl of a 33.4 mU ml$^{-1}$ Angiotensin Converti Enzyme (ACE) solution in phosphate buffered saline (PBS) pH 7.4 with a chloride concentration of 260 mM was added and the mixture was allowed to incubate for 5 minutes on a 96 well plate mixer at 700 RPM. After the incubation period 13 μl of a 0.35 mM hippuric acid-histidine-leucine (HHL) solution in PBS buffer was added and mixed for 1 minute at 700 RPM. The mixture was allowed to react for 60 minutes at 50° C. in a GC-oven. After the reaction the plate was cooled in melting ice and analysed on a flash-HPLC-column. 30 μl of the reaction mixture of each well was injected on a Chromlith Flash RP18 e 25×4.6 mm HPLC column (Merck, Darmstadt, Germany) equipped with a 10×4.6 mm RP18 e guard column from the same supplier. The isocratic mobile phase consisted of a 0.1% solution of TFA in water/acetonitrile 79/21. The eluent flow was 2 ml min$^{-1}$ and the column temperature was 25° C. The injections were performed with an interval time of 1 minute. Hippuric acid (H) and HHL were monitored at 280 nm. The peak heights of H and HHL were measured and the ACEI of each fraction was calculated according to the equation:

$$ACEIa = \frac{(DH_w - DH_a)}{DH_w * 100}$$

ACEIα Percentage inhibition of the analyte
$DH_w$ Degree of hydrolysis of HHL to H and HL in water
$DH_a$ Degree of hydrolysis of HHL to H and HL for the analyte The degree of hydrolysis (DH) was calculated by expressing the peak height of H as a fraction of the sum of the peak heights of H and HHL.

The highest activity was measured in the fractions eluting between 18 and 26 minutes. This region was collected and re-injected on a 150×2.1 mm Biosuite column with a particle size of 3 μm (Waters, Etten-Leur, the Netherlands). Mobile phase A here consisted of a 0.1% formic acid (FA) solution in Milli-Q water. Mobile phase B consisted of a 0.1% FA solution in methanol. The initial eluent composition was 100% A. The eluent was kept at 100% A for 5 minutes. After this a linear gradient was started in 15 minutes to 5% B, followed by a linear gradient in 30 minutes to 60% B. The eluent was kept at 60% B for another 5 minutes. Finally the eluent was reduced to 100% of mobile phase A in 1 minute and equilibrated for 10 minutes. The total run time was 65 minutes. The eluent flow was 0.2 ml min$^{-1}$ and the column temperature was set at 60° C. The UV trace was recorded at 215 nm. Fractions were collected from the Biosuite column at 10 seconds interval time. The fractions were split into two parts, one part was used to measure the activity using the ACE method described earlier, while the other part was used to identify the active peptides using MS and MS-MS.

Two chromatographic peaks with molecular ions of 326.2080 Da and two other peaks with molecular ions of 330.2029 Da and 318.1488 Da corresponded with the increased activities measured in the area between 18 and 26 minutes. Using MS-MS these peptides were identified as the structural isomers IPP and LPP (−0.6 ppm), ITP (−4.8 ppm) and MAP (+2.8 ppm) respectively. The protein sources of the peptides are IPP β-3-casein f74-76, LPP β-casein f151-153, ITP α-s2-casein f119-121 and MAP β-casein f102-104. IPP and LPP are reported earlier as ACEI peptides with IC50 values of 5 and 9.6 μM respectively (Y. Nakamura, M. Yamamoto, K. Sakai, A. Okubo, S. Yamazaki, T. Takano, J. Dairy Sci. 78 (1995) 777-783; Y. Aryoshi, Trends in Food Science and Technol. 4 (1993) 139-144). ITP and MAP are, to our knowledge, not earlier reported as ACEI peptides. The peptides were synthesised and the activity of each peptide was measured using a modified Matsui assay described hereafter. The IC50 values of ITP and MAP were determined to be 10 μM and 0.4 μM, respectively.

Quantification of MAP and ITP in the samples was performed on a Micromass Quattro II MS instrument operated in the positive electrospray, multiple reaction monitoring mode. The HPLC method used was similar to the one described above. The MS settings (ESI+) were as follows: cone voltage 37 V, capillary voltage 4 kV, drying gas nitrogen at 300 l/h. Source and nebulizer temperature: 100° C. and 250° C., respectively. The synthesized peptides were used to prepare a calibration line using the precursor ion 318.1 and the summed product ions 227.2 and 347.2 for MAP and using the precursor ion 320.2 and the summed product ions 282.2 and 501.2 for ITP.

ACE Activity Measurement of MAP and ITP Using a Modified Matsui Assay

This ACE inhibition activity was assayed according to the method of Matsui et al. (Matsui, T. et al. (1992) *Biosci. Biotech. Biochem.* 56: 517-518) with the modifications described below.

TABLE 1 procedure for Matsui ACE inhibition assay. The components were added in a 1.5-ml tube with a final volume of 120 μl.

| Component | Control 1 (μl) | Control 2 (μl) | Sample 1 (μl) | Sample 2 (μl) |
|---|---|---|---|---|
| HHL (3 mM) | 75 | 75 | 75 | 75 |
| H$_2$O | 25 | 45 | — | 20 |
| Sample/inhibitor | — | — | 25 | 25 |
| ACE (0.1 U/ml) | 20 | — | 20 | — |

For each sample 75 μl 3 mM hippuryl histidine leucine (Hip-His-Leu, Sigma chemicals Co.; the chemical was dissolved in 250 mM Borate containing 200 mM NaCl, pH 8.3); 20 μl 0.1 U/ml ACE (obtained at Sigma) or H$_2$O, and 25 μl sample or H$_2$O were mixed (see Table 1). The mixtures were incubated at 37° C. and stopped after 30 min by adding 125 μl 0.5 M HCl. Subsequently, 225 μl bicine/NaOH solution (1 M NaOH:0.25 M bicine (4:6)) was added, followed by 25 μl 0.1 M TNBS (2,4,6-Trinitrobenzenesulfonic acid, Fluka, Switzerland; in 0.1 M Na$_2$HPO$_4$). After incubation for 20 min. at 37° C., 4, ml 4 mM Na$_2$SO$_3$ in 0.2 M NaH$_2$PO$_4$ was added and the absorbance at 416 nm was measured with UV/Vis spectrophotometer (Shimadzu UV-1601 with a CPS controller, Netherlands).

The amount of ACE inhibition (ACEI) activity was calculated as a percentage of inhibition compared with the conversion rate of ACE in the absence of an inhibitor:

$$ACEI(\%)=(((C1-C2)-(S1-S2))/(C1-C2))*100 \quad (1)$$

wherein
C1=Absorbance without ACE inhibitory component (=max. ACE activity) [AU].
C2=Absorbance without ACE inhibitory component and without ACE (background) [AU].
S1=Absorbance in the presence of ACE and the ACE inhibitory component [AU].
S2=Absorbance in the presence of the ACE inhibitory component, but without ACE [AU].

HRS-MS Analysis of Hydrolyzed Samples

As a result, the important ACE inhibiting peptides found in PH were MAP (β-casein, pos 102-104), and ITP (α-s2-casein, pos 119-121) at a concentration of 2.85 and 1.41 mg/g, respectively (table 1). The IC$_{50}$ of MAP and ITP were determined to be 0.4 and 10 μM respectively.

Milk proteins and milk protein hydrolysates are commonly known as precursors of a large range of ACE inhibitory peptides. After consumption, the proteins and peptides are subjected to various digestive enzymatic processes in the human gastrointestinal tract, which results in the release of in-vivo ACE inhibitory peptides. In order to assess the break-down of the identified bioactive peptides and the formation of novel active peptides after human consumption, PH was processed by an artificial gastro-intestinal tract, which simulated conditions typically found in the human body. At certain times samples were taken from the GIT model system. These were also analysed using the on-line HPLC-Bioassay-MS or HRS-MS system. It showed that both MAP and ITP are of particular importance because of their high resistance against GIT digestion and their high activity therefore has very high potentials to be a blood pressure lowering peptide.

Example 1

Identification of the Novel and Potent ACE Inhibiting Tripeptides MAP and ITP in Concentrated Casein Hydrolysates To facilitate a more thorough analysis of bio-active peptides present, the casein hydrolysate obtained by the digestion with pure *A. niger* derived proline specific endoprotease and purified by acid precipitation was prepared on a preparative scale. To that end 3000 grams of potassium caseinate was suspended in 25 liters of water of 75 degrees C. After a thorough homogenisation the pH was slowly adjusted to 6.0 using diluted phosphoric acid. After cooling down to 55 degrees C., the *A. niger* derived proline specific endoproteases was added in a concentration of 4 enzyme units/gram caseinate (see Materials & Methods section for unit definition). After an incubation (with stirring) for 3 hours at 55 degrees C., the pH was lowered to 4.5 by slowly adding concentrated phosphoric acid. In this larger scale preparation the heat treatment step to inactivate the proline specific endoprotease at this part of the process was omitted. Then the suspension was quickly cooled to 4 degrees C. and kept overnight (without stirring) at this temperature. The next morning the clear upper layer was decanted and evaporated to reach a level of 40% dry matter. The latter concentrated liquid was subjected to a UHT treatment of 4 seconds at 140 degrees C. and then ultrafiltered at 50 degrees C. After germ filtration, the liquid was spray dried. This material is hereinafter referred to as Casein Derived Bio-Active Peptides (CDBAP). Using the LC/MS procedures outlined in the Materials & Methods section, the IPP, LPP and VPP content of the powdered product was determined. According to its nitrogen content, the powdered product has a protein content of about 60% (using a conversion factor of 6.38). The IPP, LPP and VPP contents of the powder are provided in Table 6. The amino acid composition of the CDBAP product is provided in Table 7. Quite remarkable is the increase of the molar proline content of the spray dried material obtained after acid precipitation: from an initial 12% to approx 24%.

TABLE 2

IPP, LPP and VPP content of CDBAP.

| IPP | LPP | VPP |
|---|---|---|
| Tripeptide content in mg/gram powder | | |
| 2.5 | 6.5 | <0.1 |
| Tripeptide content in mg/gram protein | | |
| 4.2 | 10.8 | <0.17 |

TABLE 3

Amino acid composition of the potassium caseinate starting material and CDBAP (amino acid contents after acid hydrolysis and shown as percentages of the molar amino acid content).

| Amino Acid | Starting material | CDBAP |
|---|---|---|
| Asp | 6.5 | 3.2 |
| Glu | 18.9 | 12.5 |
| Asn | — | — |
| Ser | 6.7 | 4.3 |
| Gln | — | — |
| Gly | 3.5 | 3.2 |
| His | 2.2 | 3.7 |
| Arg | 2.8 | 2.3 |
| Thr | 4.3 | 3.0 |
| Ala | 4.5 | 3.4 |
| Pro | 12.3 | 24.1 |
| Tyr | 3.9 | 2.4 |
| Val | 7.1 | 9.6 |
| Met | 2.3 | 3.9 |
| Ile | 5.0 | 4.1 |
| Leu | 9.2 | 9.0 |
| Phe | 4.0 | 3.9 |
| Lys | 6.9 | 7.4 |
| Total | 100 | 100 |

Example 2

Simulated In-Vitro Gastro-Intestinal Digestion of a Hydrolyzed Casein Protein Isolate Obtained from DSM (Delft, the Netherlands)

Digestion of protein hydrolysate (hereafter PH), a hydrolyzed casein protein isolate obtained from DSM (Delft, The Netherlands). The protein hydrolysate (PH) was prepared by incubation of 10 wt % potassium caseinate with overproduced and essentially pure endoprotease from *Aspergillus niger* as described in WO 02/45524.

The digestion procedure was performed using a dissolution model (Vankel) with a 100 ml flask. The temperature of the water bath was set to 37.5° C. and the paddle speed was chosen such that the sample was kept in suspension (100 rpm).

About 3.4 grams of PH (protein level of 59%) was dissolved/suspended in 100 ml Milli-Q water. During gastric simulation 5 M HCl was used to decrease the pH, at the end of gastric simulation and during the duodenal phase 5 M NaOH was used to raise the pH.

The protein hydrolysate suspension was preheated to 37.5° C. At t=0 min 0.31 g of pepsin (Fluka order no. 77161) was suspended separately in 5 ml of the sample and was directly added.

The pH was adjusted slowly by hand using a separate pH meter according to the following scheme;
t=20 min pH decreased to 3.5
t=40 min pH to 3.0
t=50 min pH to 2.3
t=60 min pH to 1.8
t=65 min pH raised to 2.7
t=75 min pH to 3.7
t=80 min pH to 5.3

At t=90 min 0.139 g of 8 times USP pancreatin (Sigma order no. P7545) was suspended separately in 5 ml of the sample and was directly added;
t=93 min pH to 5.5
t=95 min pH to 6.3
t=100 min pH to 7.1

The experiment was stopped at t=125 min and the pH was checked (was still pH 7).

The samples were transferred into a beaker and were heated in a microwave till boiling. Subsequently, the samples were transferred into glass tubes and incubated at 95° C. for 60 min. This is necessary to inactivate all protease activity. After cooling the samples were put in falcon tubes and centrifuged for 10 min at 3000×g. The supernatant was freeze dried. The total N concentration was determined and converted to protein level using the Kjeldahl factor of casein (6.38). The protein level of the PH digest was 48.4%.

TABLE 4

Results of example 1. Concentration of MAP and ITP in PH and in the digested product in an artificial human gastro intestinal tract (mg/L).

| | Concentration in µg g$^{-1}$ powder | |
|---|---|---|
| Sample | MAP | ITP |
| PH in example 1 | 2851.4 | 903.74 |
| PH after digestion | 3095.8 | 889.13 |

TABLE 5

ACE inhibition (IC50 values) of MAP, ITP and IPP, the values determined by the at-line ACE assay and the modified Matsui assay.

| | IC50 value in µM | |
|---|---|---|
| Peptide | At-line ACE assay | Modified Matsui assay |
| MAP | 3.8 | 0.4 |
| ITP | 50 | 10 |
| IPP (reference) | 7.1 | 2 |

Example 3

Simulated In-Vitro Gastro-Intestinal Digestion of Synthetic MAP and ITP

In order to measure stability of the peptides in the gastrointestinal tract (GI) micro-dissolution was used. This following test was used to test the GI stability of MAP and ITP.
Components:
For the dissolution the following solutions were used:
0.1 mol/l HCl
1 mol/l NaHCO3
Simulated Gastric Fluid;
1.0 g sodium chloride en 3.5 ml 0.1 mol/l HCl in 500 ml water (degassed in sonification bath, 10 min.)
Enzymes Gastric Conditions (Amounts Needed in 1 Ml Total Volume):
2.9 mg Pepsine en 0.45 mg Amano Lipase-FAP15 in 50 µl simulated gastric fluid
Enzymes Intestinal Conditions (Amounts Needed in 1 ml Total Volume):
9 mg Pancreatine (Sigma P8096) en 0.125 mg bile extract in 50 µl 1.0 mol/l NaHCO3

Procedure:

Gastric Conditions:

Each vial was filled with:

0.82 ml simulated gastric fluid+70 μl MilliQ+10 μg (10× diluted) Mixture 1, take a sample when T=37.5° C. (t=0), add 50 μl pepsine/lipase mixture (shake).

The pH is measured and adjusted to 3.5 with 0.1 mol/l HCl

Incubation for 60 minutes, after 60' a sample is taken.

Intestinal Conditions:

50 μl pancreatine mixture is added, the pH is measured and adjusted to 6.8 with

HCl.

Samples are taken at 5', 30' en 60' after the addition of pancreatine (shake).

All samples are kept at 95° C. for 60 minutes to stop the enzyme from being active.

After cooling the samples were stored at −20° C. until analysis.

The samples were centrifuged and analyzed with HPLC-MRM-MS. (For VAWWMY much more energy was needed to fragment it, in order to measure it. This was necessary because of the largeness of the peptide.)

Insel IS89 was used (gently shaking at 0), which is an incubation device meant for 96 wells plates.

For tables 6 and 7 the measured concentration of the peptide is given in ng/ml, calculated to the relative concentration of MAP.

TABLE 6

Simulated in-vitro gastro-intestinal digestion of synthetic MAP-1 microgram/ml

| Time (min) | a conc | b Ng/ml | % remaining trial 1 | % remaining trial 2 | % average |
|---|---|---|---|---|---|
| 0 | — | 2962.5 | 100 | 100 | 100 |
| 30 | — | 2760 | — | 93 | 93 |
| 60 | 1902.6 | — | 64 | — | 62 |
| 65 | 1384.6 | 1654.1 | 47 | 56 | 51 |
| 75 | 2282.2 | 1608.3 | 43 | 54 | 49 |
| 90 | 730.5 | 911.6 | 25 | 31 | 28 |
| 120 | 377.2 | 503.3 | 13 | 17 | 15 |

Where - is indicated this denotes that measurements were not taken.

TABLE 7

Simulated in-vitro gastro-intestinal digestion of synthetic MAP-10 microgram/ml

| Time (min) | a conc | b Ng/ml | % remaining trial 1 | % remaining trial 2 | % average |
|---|---|---|---|---|---|
| 0 | — | 82499.2 | 100 | 100 | 100 |
| 30 | 50635.6 | 76600.6 | 61 | 93 | 77 |
| 65 | 28492.5 | 33339.1 | 35 | 40 | 37 |
| 75 | 21936.4 | 21991.9 | 27 | 27 | 27 |
| 90 | 7588.3 | 10490.8 | 9 | 13 | 11 |
| 120 | 2810.6 | 2661.8 | 3 | 3 | 3 |

Where - is indicated this denotes that measurements were not taken.

TABLE 8

Simulated in-vitro gastro-intestinal digestion of synthetic ITP-1 microgram/ml

| Time (min) | a conc | b Ng/ml | % remaining trial 1 | % remaining trial 2 | % average |
|---|---|---|---|---|---|
| 0 | 1325.201 | 901.297 | 100 | 100 | 100 |
| 30 | 1236.423 | 952.165 | 93 | 106 | 99 |
| 60 | 950.665 | 893.015 | 72 | 99 | 85 |
| 65 | 722.452 | 677.991 | 55 | 75 | 65 |
| 75 | 707.693 | 698.078 | 43 | 77 | 65 |
| 90 | 603.143 | 704.863 | 46 | 78 | 62 |
| 120 | 701.749 | 678.751 | 53 | 75 | 64 |

Where - is indicated this denotes that measurements were not taken.

TABLE 9

Simulated in-vitro gastro-intestinal digestion of synthetic ITP-10 microgram/ml

| Time (min) | a conc | b Ng/ml | % remaining trial 1 | % remaining trial 2 | % average |
|---|---|---|---|---|---|
| 0 | 11230.3 | 9388.467 | 100 | 100 | 100 |
| 30 | 8725.687 | 7884.828 | 78 | 84 | 81 |
| 60 | 8542.271 | 9951.495 | 76 | 106 | 91 |
| 65 | 6739.74 | 8504.414 | 60 | 91 | 75 |
| 75 | 7016.45 | 6052.258 | 62 | 64 | 63 |
| 90 | 7212.26 | 5660.004 | 64 | 60 | 62 |
| 120 | 5168.85 | — | 46 | — | 46 |

Where - is indicated this denotes that measurements were not taken.

These results demonstrate that the tripeptide MAP exhibits reasonably good stability under gastro-intestinal conditions especially after 1 hour under stomach conditions. However, it does undergo further degradation before reaching the end of the gut. It is believed that MAP is protected against this degradation in the presence of other peptides within the casein hydrolysate; this explains the apparent differences in stability for MAP shown in examples 2 and 3.

The results also demonstrate the excellent stability under gastro-intestinal conditions of ITP. This excellent stability compensates for the somewhat lower potency of ITP as an ACE inhibitor compared to MAP.

Example 4

Preparation of Fermented Milk Containing Map and ITP

Preculture Preparation:

Sterile skimmed milk (Yopper ex Campina, Netherlands) was inoculated for 24 hours at 37° C. with 2 to 4% of a culture of a *Lactobacillus delbruecki* subsp. *Lactis* 05-14 (deposited at the Centraal Bureau voor Schimmelculturen (CBS), Netherlands, on 26 Jan. 2001 and having number CBS 109270) that had been stored at −80° C. as a full grown culture in the above described skimmed milk, diluted with sterile 10% glycerol to an end concentration of 6% glycerol. The resulting product is designated as preculture.

The strain was characterized by an API50CHL strip. The strain was able to ferment D-glucose, D-fructose, D-mannose, N-acetyl glucosamine, maltose, lactose, sucrose and trehalose. According to the APILAB Plus databank (version 5.0) it was subsequently identified as *Lactobacillus del-*

*brueckii* subsp. *lactis*. The API50CHL strip and databank are available from bioMerieux SA, 69280 Marcy-l'Etoile, France.

Fermentation:

Reconstituted milk of 4.2% MPC-80 (Campina, Netherlands), 0.5% lactose and 0.3% Lacprodan 80 (Campina, Netherlands), was pasteurised for 2 min at 80 degrees. The milk was fermented with 2 wt % of the preculture *Lactobacillus delbruecki* subsp. *Lactis* 05-14. The fermentation was performed in 150 ml jars under static conditions and performed without pH control at 40° C.

After 24 hours a sample was taken and centrifuged for 10 min at 14.000 g. The pH was 5.3 and the MAP concentration 18.3 mg/L. ITP could not be found in the fermented milk.

Example 5

Muffin Comprising Blood Pressure Lowering Protein Hydrolysate

The MAP and ITP containing compositions according to the invention can be incorporated into a variety of products including food products. To illustrate its use in a popular pastry product, the ACE inhibiting peptides were incorporated into a muffin.

A muffin batter was prepared by first combining the following dry ingredients: 500 grams of wheat flour (Reiger from Meneba, The Netherlands), 141 grams of whole egg powder, 4.7 grams of egg white powder, 35.2 grams of dextrose, 470 grams of sucrose, 2.4 grams of emulsifier (in this case Admul 5306 of Quest, The Netherlands), 4.7 grams of salt, 7 grams of sodium bicarbonate, 9.4 grams of pyrophosphate, 1.6 grams of citric acid and 3.5 grams of sorbic acid. To this the MAP and ITP containing CDBAP powder was added to reach a final concentration of 10 grams of CDBAP powder per kg of batter. Then all dry ingredients were thoroughly mixed.

To this dry mix 475 grams of water and 475 grams of vegetable oil was added and powder and liquids were mixed for 7 minutes in speed 1 of a Hobart mixer. The resulting batter was poured into muffin trays with each individual muffin mould containing approx. 50 grams of batter. The trays were baked for 23 minutes at 195-200 degrees C. The crusts of the resulting muffins were slightly darker than the crusts of reference muffins baked without CDBAP powder added. However, the consistencies of both types of muffins were identical.

On the basis of its CDBAP content, each one of the muffins thus obtained contains approx 0.5 grams of CDBAP representing approx half of the desired daily dosage of ACE inhibiting peptides for a hypertensive person.

The invention claimed is:

1. A food product comprising a food or a food ingredient and an amount of 1 mg/kg or more of the tripeptide ITP effective to inhibit angiotensin converting enzyme.

2. The food product according to claim 1, wherein the amount of tripeptide ITP is 3 mg/kg or more.

3. The food product according to claim 1, also comprising the tripeptide MAP, wherein the amount of the tripeptide MAP is 1 mg/kg or more and the amount of tripeptide ITP is 6 mg/kg or more.

4. The food product according to claim 1, wherein the amount of the tripeptide ITP is 12 mg/kg or more.

5. The food product according to claim 4, futher comprising the tripeptide MAP in an amount of from 5 mg/kg to 20 mg/kg or more.

6. The food product according to claim 1, further comprising 50-200 mmol/kg $K^+$ and/or 15-60 mmol/kg $Ca^{2+}$ and/or 6-25 mmol/kg $Mg^{2+}$.

7. The food product according to claim 6, wherein the $K^+$ is in an amount of 110-135 mmol/kg and/or the $Ca^{2+}$ is in an amount of 35-45 mmol/kg and/or the $Mg^{2+}$ is in an amount of 13-20 mmol/kg.

8. The food product according to claim 1, further comprising one or more B-vitamins.

9. The food product according to claim 8, comprising folic acid, Vitamin B6 and vitamin B12.

10. The food product according to claim 1, further comprising 3 to 25 wt % sterol.

11. The food product according to claim 4, wherein the amount of the tripeptide ITP is in an amount from 25 mg/kg to 100 mg/kg.

12. The food product according to claim 5, wherein the amount of the tripeptide MAP is from 5 mg/kg to 20 mg/kg or more and the amount of the tripeptide ITP is from 25-100 mg/kg.

13. The food product according to claim 10, wherein the amount of sterol is from 7 to 15 wt %.

* * * * *